United States Patent [19]

Lawrence et al.

[11] 4,155,331
[45] May 22, 1979

[54] METHOD FOR CRYOPRESERVATION OF MULTICELLULAR ORGANISMS

[76] Inventors: Addison L. Lawrence, 11011 Renwick; John G. Baust, 4367 Faculty, both of Houston, Tex. 77035

[21] Appl. No.: 783,937

[22] Filed: Apr. 1, 1977

[51] Int. Cl.² .................. A01K 61/00; F25D 17/02
[52] U.S. Cl. ..................................... 119/2; 62/64
[58] Field of Search ............... 62/62, 64, 78; 119/2; 128/1 R

[56] References Cited

U.S. PATENT DOCUMENTS

| | | | |
|---|---|---|---|
| 3,303,662 | 2/1967 | Moline et al. | 62/62 |
| 3,677,024 | 7/1972 | Segall | 128/1 R |
| 3,850,143 | 11/1974 | Hirono | 119/2 |
| 3,940,943 | 3/1976 | Sikes et al. | 62/64 |

OTHER PUBLICATIONS

Cowley et al., "Ultra Rapid Cooling Techniques in the Freezing of Biological Materials", Feb. 16–18, 1961, pp. 6–7.

*Primary Examiner*—Jay N. Eskovitz
*Assistant Examiner*—Robert P. Swiatek
*Attorney, Agent, or Firm*—Arnold, White & Durkee

[57] ABSTRACT

A method for the cryopreservation of multicellular organisms characterized by rapid cooling and warming rates, exceeding 100° C. per minute, to achieve 80% survival after storage in the frozen state. The method involves exposing multicellular organisms to a cryoprotectant medium, freezing the organisms and medium by cooling at a rate greater than 100° C. per minute, holding the organisms and medium at a point below 0° C. for a period of time, and cooling the organisms and the medium at a rate greater than 100° C. per minute to an appropriate storage temperature depending upon the desired length of the storage period. The method is more specifically described with regard to aquatic organisms, and particularly described with regard to the cryopreservation of immature marine crustaceans.

17 Claims, No Drawings

METHOD FOR CRYOPRESERVATION OF MULTICELLULAR ORGANISMS

BACKGROUND AND PRIOR ART

This invention relates to the field of cryopreservation of living cells; and more particularly, a method is provided for the cryopreservation of multicellular organisms.

Cryopreservation in its broadest sense would include preservation at above freezing temperatures, as is commonly done in blood banks. However, in the context of this invention, the meaning of the word is restricted to the preservation of living cells at below freezing temperatures.

The field of cryopreservation had its inception in the early attempts to store blood cells at low temperatures. Experiments directed at preserving blood in the frozen state have been documented as early as 1939. (For an historical survey on the cryopreservation of blood cells, see CRYOBIOLOGY, Vol. 6, No. 5, 1970.) Since the early experiments with blood, researchers have expanded the idea of preserving living cells to various other types. Consequently, with such expansion, the field of cryopreservation has developed as a new technology aimed at the preservation of living cells by storing in the frozen state with subsequent revival.

For the most part, cryopreservation of living cells has dealt with single cells only. As reported by D. G. Whittlingham, S. P. Leibo and P. Mazur of the Biology Division of Oak Ridge National Laboratory in an article in SCIENCE, Vol. 178, October 1972, attempts to freeze multicellular mammalian embryos and revive them to survival have met with limited success. The article "Survival of Mouse Embryos Frozen to −196° and −269° C." by the above named authors was an attempt to investigate the mechanisms of freezing injury to multicellular systems and ascertain the critical cryobiological factors. The experiment was conducted on mouse embryos, and the researchers concluded that the cryobiological factors that might influence the survival of frozen multicellular organisms are primarily the suspending medium, cooling rate, final temperature, and warming rate.

In the method of cryopreservation taught by the article, the freezing rate for survival of the organism is required to be slow, between 0.3° and 2° C. per minute, and warming rates should be from 4° to 25° C. per minute. Storage of the frozen embryos was at −196° C. for several days. The cryoprotectant used was dimethyl sulfoxide (DMSO).

It has been generally accepted and practiced by workers in the field of cryopreservation of living cells that a slow cooling rate below freezing of about 1° C. per minute is required for survival of the cells. Meryman in *Annals of the New York Academy of Sciences*, Vol. 85, pp. 503–509 (1960) opined that rapid freezing would not work for animal tissues.

With regard to the suspending medium or cryoprotectant, glycerol and dimethyl sulfoxide (DMSO) have been found to be most effective, with about 5% to 15% concentration being commonly used. (See Paul, *Cell and Tissue Culture*, 4th Ed., pp. 308–315 (1970)). A third type of cryoprotectant that has been used is polyvinylpyrrolidone (PVP), and a fourth type is dextrose (glucose) and/or sucrose. A discussion of the combined effects of freezing rates and various cryoprotective agents on the preservation of human erythrocytes is presented in *CRYOBIOLOGY*, Vol. 4, No. 5 (1968) authored by Rapatz and Leyet. One of the summary conclusions drawn by these researchers is that glycerol and DMSO are effective in preventing lysis at low cooling rates, but are injurious at high cooling rates.

Methods of cryopreservation used have generally involved first suspending the cells or organism in a liquid cryoprotectant medium suitable for freezing, usually a solution containing about 5% to about 15% DMSO or glycerol. Next, the cell suspensions are frozen slowly at a rate of about 1° C. per minute and maintained at a storage temperature of −70° C. or lower. For revival, the frozen cell suspension is thawed, and the cells are separated from the cryoprotectant medium.

Specific methods of cryopreservation are presented in U.S. Pat. No. 3,943,993 (Smith) entitled "Low Temperature Storage of Surface Attached Living Cell Cultures," U.S. Pat. No. 3,940,943 (Sikes) entitled "Multistage Freezing System for Preservation of Biological Materials," and U.S. Pat. No. 3,303,662 (Moline) entitled "Process for Cell Preservation."

Smith relates to a process for cooling, storing and reviving surface attached living cell cultures. The process involves preparing an attached cell culture and exposing the cells to a storage medium containing about 10% dimethyl sulfoxide. The temperature is lowered at a rate of 1° C. per minute until about −20° C. or lower is reached. The cell cultures are then transferred to a container having a temperature of about −70° C. or less, where the cells are kept until time to withdraw them for revival. The cells are warmed and the storage medium is replaced by an appropriate cell culture medium.

Sikes relates to a freezing and thawing process for the preservation of animal semen, blood and other biological materials. In the process described, a sample of semen is placed in a cryoprotective agent and cooled slowly from body temperature to +5° C. and held there for 30 minutes or longer. The temperature is rapidly lowered to a temperature slightly below freezing and held for one to eight minutes. The temperature is then taken down to −100° C. at a rate of 20° C. per minute. The sample is then immersed into liquid nitrogen for final cooling and storage. To revive the cells, the sample and protective agent are thawed by immersion in +45° C. water.

The process described in Moline is one for preserving animal organs. In the process, the organ is perfused by a protective agent and cooled to the freezing point. The organ is further cooled through the liquid-solid phase change in less than ten minutes, with cooling of the organ to about −50° C. at a rate of not more than about 3° C. per minute. The organ is further cooled to a temperature at or below −130° C. where it is maintained.

All of the above described methods, though dealing with various types of cellular arrangements, follow a basic theory that cryopreservation techniques must be conducted with a slow cooling rate below the freezing point in order to achieve survival of the cells after thawing. Also, the methods have all used cells or tissues from terrestrial mammals.

SUMMARY OF THE INVENTION

With the present invention, there is provided a method of cryopreservation for cooling, storing in a frozen state, and reviving living cells, particularly multicellular organisms. A method of cryopreservation of living multicellular organisms in accordance with this invention comprises the steps of exposing the organisms to a cryoprotectant medium, cooling the organisms and the medium to freezing at a rapid cooling rate averaging greater than 100° C. per minute, holding the organisms and medium at a temperature below 0° C. for a period of time, and cooling the organisms and the medium at a rate greater than 100° C. per minute to an appropriate storage temperature depending upon the desired length of the storage period. The method continues with the organisms and the medium being maintained at the storage temperatures until the organisms are desired to be revived, whereupon the organisms and the medium are warmed at a rapid warming rate greater than 100° C. per minute.

Accordingly, one aspect of the invention is based on the theory that extremely rapid cooling and warming rates, exceeding 100° C. per minute, are to be used to achieve survival of multicellular organisms after storage in the frozen state. It is in this aspect that the method of this invention is most clearly distinguished from the cryopreservation art now practiced which teaches the use of slow cooling and warming rates of approximately 1° per minute.

In its more specific aspects, the method of the present invention uses a cryoprotectant medium of 5-20% glycerol and 0-5% glucose; dimethyl sulfoxide and polyvinylpyrrolidone can also be used as a cryoprotective agent. Freezing of the multicellular organisms and the cryoprotectant medium by cooling at a rate of 100° C. per minute to 2000° C. per minute with a storage temperature of −80° C. or lower have been found effective in promoting survival of multicellular organisms stored in the frozen state. Subsequent to the series of steps which involve the storage of the multicellular organisms, and after the desired storage period, the organisms can be revived by warming to just below 0° C. at a rate of 100°–800° C. per minute, and then warming at a rate of about 10° C. per minute.

It is a primary feature of this invention to provide a method of cryopreservation for living multicellular organisms, with survival of the organisms upon revival from the frozen state. One of the important attributes of the present invention is that a method of cryopreservation is provided which assigns a range of values for the cryobiological factors that influence the survival of frozen multicellular organisms in order to achieve satisfactory recovery of living organisms from the frozen state. With the method of this invention, it is now possible to achieve cryopreservation of multicellular systems.

The method of this invention provides the ability to preserve multicellular mammalian systems such as tissues and organs by freezing. Also, the ability is provided to preserve viable embryos by freezing them to low temperatures, which has applications in genetics and developmental biology.

The ability to preserve embryos by freezing, in addition to the above applications, would be useful in enhancing food production by providing "seed stock" during periods of inadequate supply. The contribution of the method of cryopreservation for living multicellular organisms of this invention represents an especially important contribution to the conservation of aquatic life to insure the production and harvest of aquatic crops at times when a sufficient supply is not available from natural sources. For example, the shrimp maricultural is limited because "seed stock" is available only on a seasonal basis. By cryopreservation of shrimp larvae, which can later be used as seed stock in ponds, shrimp can be made available on a twelve month basis.

Accordingly, it is a further feature of this invention to provide a method of cryopreservation for successfully storing in the frozen state and reviving to survival multicellular invertebrate aquatic organisms. The method may be applied to both fresh and salt water aquatic life.

Generally, the method of cryopreservation for multicellular invertebrate aquatic organisms comprises the steps of: acclimating the organisms from native ambient conditions to a temperature several degrees above freezing by cooling, instantaneously chilling the organisms with water of a temperature near 0° C., exposing the organisms to a cryoprotectant medium, freezing the organisms by cooling at a rate greater than 100° C. per minute, holding the organisms at a temperature below 0° C. for a period of time, and cooling the organisms at a rate greater than 100° C. per minute to an appropriate storage temperature depending upon the desired length of storage time. After storing the organisms in a frozen state at a low temperature for a period of time, the organisms can be revived to survival by rewarming to a temperature below, but near, 0° C. at a rapid rate of warming, and warming the organisms from that point to a temperature near the acclimating temperature at a slower warming rate.

In its more specific aspects, the method of cryopreservation for multicellular invertebrate aquatic animals involves acclimating the organisms to about 15°–25° C., by cooling with water at the rate of 1° C. per hour. If the aquatic organisms are saltwater organisms, the salinity of the water should be taken to 25–40 °/$_{oo}$ (parts per thousand) at a rate of 1 °/$_{oo}$ per hour. Following acclimation, the organisms are instantaneously chilled with −1°. to −2° C. water; if saltwater is required, the salinity should be in the range of 0–40 °/$_{oo}$. Exposure of the organisms to a cryoprotectant medium is for 20–30 minutes at a temperature of −1° C. to −2° C. The cryoprotectant can be a solution having a 5–20% glycerol concentration, and may include 0–5% glucose. Dimethyl sulfoxide and polyvinylpyrrolidone can also be used. After exposure of the organisms to the cryoprotectant medium, the organisms are frozen by cooling at a rate greater than 100° C. per minute to a temperature of −15° to −40° C., where the organisms are held for 5–30 minutes. The organisms are next cooled instantaneously to the storage temperature, generally −80° C. or colder.

At the end of the storage period, when revival is desired, the organisms are warmed to a temperature just below 0° C. at a rate between 100° C. and 800° C. per minute. The organisms are rinsed with water at a temperature of 15°–25° C. to further warm them. If marine animals are used, the salinity should be 26–30 °/$_{oo}$ seawater. Following rinsing, the organisms are warmed to a temperature of 23°–26° C. at a rate of about 10° C. per minute.

Utilizing the method of the present invention to freeze and store shrimp nauplii, a post thaw survival exceeding 80% has been attained.

DESCRIPTION OF A PREFERRED EMBODIMENT

A. General Discussion

The present invention provides a method for preserving living cells over extended periods of time at low temperature. The term "multicellular organism," as used herein, includes living systems such as zygotes, and the early developmental stages of animals, but excludes isolated body fluids, blood, and animal tissue culture preparations. The process of this invention is generally applicable to the preservation of multicellular organisms of any animal, though it is especially applicable to multicellular invertebrate animals and preferably to aquatic invertebrates.

Generally, the method of this invention comprises the steps of (1) exposing the organisms to a cryoprotectant medium, (2) cooling the organisms and medium combination to a temperature below freezing at a rapid cooling rate greater than 100° C. per minute, (3) holding the organisms and medium combination at a temperature below freezing for a period of time, and (4) cooling the organisms and medium combination to the storage temperature at a cooling rate greater than 100° C. per minute.

A number of compounds can be used for the cryoprotectant medium. Among those contemplated for use in the method just outlined are: polyhydroxy alcohols, aldehydes and ketones, such as glycerol, glucose and fructose. Also, dimethylsulfoxide (DMSO) and polyvinylpyrrolidone could be used, though they are not preferred. A combination of two or more of these cryoprotective agents can also be used. The cryoprotectants should be utilized in a total concentration with the range of 5 to 15% of the weight/volume.

In direct contradiction to the cryopreservation art heretofore used which teaches and reports the inability to freeze multicellular organisms by cooling at a rapid rate and achieve satisfactory recovery statistics, the method of the present invention utilizes cooling rates greater than 100° C. per minute. The multicellular organisms and cryoprotectant combination are first cooled at a rate of cooling greater than 100° C. per minute to freezing, that is, where the change of phase from liquid to solid is completed. The exact temperature at which complete solidification occurs will vary somewhat with the particular system involved, but in general solidification will have occurred by attaining a temperature of −50° C. This may be achieved by conventional methods, for example, by immersion in a liquid refrigerant such as liquid nitrogen or by passing refrigerated gas over the combination. Apparatus commercially available for freezing biological substances by these methods is a programmable freezing system manufactured by Cryo-med of Michigan.

The multicellular organisms are held at a temperature below the freezing point of the solution for a period of time before further cooling. The range of the temperature and of the time period will be referred to as the "survival window." The survival window may be from −15° C. to −50° C. in temperature, and between 10 and 60 minutes in duration.

Cooling of the frozen system (organisms and madium) from the survival window to storage temperature is also at a rate greater than 100° C. per minute. The storage temperature will be selected based upon the desired length of storage. A storage temperature of −70° C. is adequate for short duration storage periods, but for longer storage periods, temperatures below about −130° C., though not lower than about −200° C. are recommended. Apparatus using liquid nitrogen as the refrigerant are commercially available for use in freezing biological substances and for storing frozen biological substances at temperatures from −70° C. to −196° C.

When the multicellular organisms preserved by the method of this invention are desired to be revived, the frozen organisms - medium combination is thawed. Warming from the storage temperature to the freezing point of the combination is at a rate greater than 100° C. per minute, though not exceeding 800° C. per minute. Although the freezing point temperature will vary, raising to a temperature of −1° C. will generally be adequate. The organisms are then rinsed in a warm water bath which is at about 15°-20° C. The organisms are then warmed to a temperature of about 25° C. at a rate of about 10° C. per minute. The thawed organisms can then be cultured for growth or undergo processing depending upon the intended use.

B. Example

To better illustrate and particularize the method of the present invention, a specific adaptation of the method to the cryopreservation of multicellular invertebrate aquatic organisms will be presented.

The method of the present invention applied to the cryopreservation of aquatic organisms comprises the steps of:

(a) acclimating the organisms from native ambient conditions to about 15° to 25° C. by cooling;

(b) chilling the organisms with a fluid medium maintained at a temperature near 0° C.;

(c) exposing the organisms to a cryoprotectant medium for a period of time at a temperature just below 0° C.;

(d) freezing the organisms and protective medium by cooling at a rate greater than 100° C. per minute;

(e) holding the organisms between −15° C. and −50° C. for 10 to 60 minutes; and (f) cooling the organisms and protective medium to an appropriate storage temperature at a rate greater than 100° C. per minute.

In the above method, cooling in step (a) is at a rate of about 1° C. per hour. Chilling of the organisms in step (b) is with water that is maintained at a temperature of −1° C. to −3° C. The cryoprotectant medium comprises 10-15% glycerol and 0-5% glucose, with exposure being for 20 to 30 minutes at −1° C. to −2° C. After freezing, the organisms are held in step (c) between −15° C. and −50° C. for 10 to 60 minutes. The storage temperature is −80° C. or colder, but not to go below −200° C.

At the end of the storage period, the method of cryopreservation further comprises the steps of warming the organisms to a temperature just below 0° C. at a rate between 100° C. and 800° C. per minute, followed by rinsing of the organisms with water at a temperature of 15°-25° C. Finally, the organisms are warmed to a temperature of at least 20° C. at a rate of about 10° C. per minute.

To provide a more particular example of the method, its application to the cryopreservation of shrimp is presented. In their development, shrimp pass through a series of stages. In one of the most important and best-known species of the genus Penaeus, the *Penaeus setiferus*, the eggs hatch into an early developmental stage, called the nauplius, and sequentially molt to an adult form. Although the method can be used in any stage of development from zygote to post-larvae, the nauplius appears to be the most advantageous commercially.

Also, the method may be used with the genus *Meta penaeus*.

The method of the invention in this application utilizes shrimp nauplii received from a shrimp hatchery and comprises the steps of:

(a) acclimating the shrimp from native ambient conditions to 15°-20° C. and 25-30 °/$_{oo}$ salinity sea water by cooling at a rate of 1° C. per hour and changing salinity at a rate of 1 °/$_{oo}$ per hour;

(b) chilling the shrimp with −1° C. to −2° C. sea water of 25-30 °/$_{oo}$ salinity;

(c) exposing the shrimp to a cryoprotectant medium comprising glycerol and glucose in concentrations of 10-15% and 0-5% weight/volume, respectively, of total solution; the exposure being for 20-30 minutes at −1° C. to −2° C.;

(d) freezing the shrimp and protective medium by cooling at a rate greater than 100° C. per minute;

(e) holding the shrimp between −15° C. and −50° C. for a period of 10 to 60 minutes; and (f) cooling the shrimp to a storage temperature of −80° C. or colder at a rate greater than 100° C. per minute.

Thawing is by warming of the shrimp to −1° C. at rates between 100° and 800° C. per minute followed by rinsing with 15°-20° C. and 25-30 °/$_{oo}$ salinity sea water. Thereafter, the shrimp are warmed to 23° C. to 30° C. at a rate of about 10° C. per minute.

The post thaw survival is in excess of 80%.

The foregoing description of the invention has been directed to a particular preferred embodiment in the form of an example of its application for the purpose of explanation and illustration. It will be apparent to those skilled in this art that the invention admits to many applications, each of which requiring modifications and changes in the preferred method presented, but which do not depart from the scope of this invention. For example, the method of this invention can be used not only for temperate and polar, but also tropical multicellular organisms. It is applicant's intention to cover all such applications, variations and equivalents as fall within the scope of the invention.

What is claimed is:

1. A method for the cryopreservation of multicellular organisms comprising the steps of:
   exposing the multicellular organisms to a cryoprotectant medium;
   freezing the organisms and medium by cooling at a rate greater than 100° C. per minute;
   holding the organisms and medium at a temperature below 0° C. for a period of time; and
   cooling the organisms and the medium at a rate greater than 100° C. per minute to an appropriate storage temperature depending upon the length of the storage period.

2. The method of claim 1 wherein said cryoprotectant medium comprises from 5-20% glycerol and 0-5% glucose by weight per volume.

3. The method of claim 1 wherein said storage temperature is lower than −80° C.

4. The method of claim 1 wherein said organisms are held at a temperature of −15° C. to −50° C. for 10 to 60 minutes.

5. The method of claim 1 including the revival of the frozen organisms which comprises the steps of:
   warming the organisms to a temperature just below 0° C. at a rate greater than 100° C. per minute;
   rinsing the organisms with water maintained at a temperature above 0° C.; and
   warming the organisms to a temperature above 0° C. at a rate of about 10° C. per minute.

6. The method of claim 5 wherein said organisms are initially warmed to −1° C.

7. The method of claim 5 wherein said organisms are rinsed with water at a temperature of 15°-20° C.

8. The method of claim 5 wherein said organisms are warmed to a temperature of 20°-30° C.

9. A method for the cryopreservation of multicellular invertebrate aquatic organisms comprising the steps of:
   acclimating the aquatic organisms from native ambient conditions to a temperature several degrees above freezing by cooling;
   instantaneously chilling the aquatic organisms with water at a temperature near 0° C.;
   exposing the aquatic organisms to a cryoprotectant medium;
   freezing the aquatic organisms by cooling at a rate greater than 100° C. per minute;
   holding the aquatic organisms at a temperature below 0° C. for a period of time; and
   cooling the aquatic organism at a rate greater than 100° C. per minute to an appropriate storage temperature depending upon the length of time that the organisms are to be stored in the frozen state.

10. The method of claim 9 wherein acclimation of the aquatic organisms is to a temperature of about 15°-20° C. by cooling at a rate of 1° C. per hour.

11. The method of claim 9 wherein the aquatic organisms are chilled with water at −1° C. to −3° C.

12. The method of claim 9 wherein the cryoprotectant medium comprises 10-15% glycerol and 0-5% glucose by weight to volume, with exposure being for 20 to 30 minutes at a temperature of −1° C. to −2° C.

13. The method of claim 9 wherein the organisms are held between −15° C. and −50° C. for 10 to 60 minutes.

14. The method of claim 9 wherein the storage temperature is −80° C.

15. The method of claim 9 including the revival of the frozen aquatic organisms which comprises the steps of:
   warming the organisms to a temperature just below 0° C. at a rate greater than 100° C. per minute;
   rinsing of the aquatic organisms with water at a temperature of 15°-25° C.; and
   warming the aquatic organisms to a temperature of at least 20° C. at a rate of about 10° C. per minute.

16. A method for the cryopreservation of shrimp nauplii comprising the steps of:
   acclimating the shrimp from native ambient conditions to 15°-20° C. and 25-30 °/$_{oo}$ salinity sea water by cooling at a rate of 1° C. per hour and changing salinity at a rate of 1 °/$_{oo}$ per hour;
   chilling the shrimp with −1° C. to −2° C. sea water of 25-30 °/$_{oo}$ salinity;
   exposing the shrimp to a cryoprotectant medium comprising glycerol and glucose in concentrations of 10-15% and 0-5% weight/volume, respectively, of total solution; the exposure being for 20-30 minutes at −1° C. to −2° C.;
   freezing the shrimp and protective medium by cooling at a rate greater than 100° C. per minute;
   holding the shrimp between −15° C. and −50° C. for a period of 10 to 60 minutes; and cooling the shrimp to a storage temperature of −80° C. or colder at a rate greater than 100° C. per minute.

17. The method of claim 16 including the revival of the frozen shrimp nauplii which comprises the steps of:

warming the shrimp to −1° C. at a rate between 100° C. per minute and 800° C. per minute;

rinsing the shrimp with 15°–20° C. and 25–30 ‰ salinity sea water; and warming the shrimp to 23°–26° C. at a rate of about 10° C. per minute.

* * * * *